(12) United States Patent
McDonald

(10) Patent No.: US 10,898,322 B2
(45) Date of Patent: Jan. 26, 2021

(54) TAVR VALVE GUIDEWIRE AND GUIDETUBE WITH ADJUSTABLE DISTAL LOOP

(71) Applicant: Michael B. McDonald, Cordova, TN (US)

(72) Inventor: Michael B. McDonald, Cordova, TN (US)

(*) Notice: Subject to any disclaimer, the term of this patent is extended or adjusted under 35 U.S.C. 154(b) by 147 days.

(21) Appl. No.: 15/445,272

(22) Filed: Feb. 28, 2017

(65) Prior Publication Data

US 2017/0245990 A1 Aug. 31, 2017

Related U.S. Application Data

(60) Provisional application No. 62/301,270, filed on Feb. 29, 2016.

(51) Int. Cl.
*A61F 2/24* (2006.01)
*A61M 25/00* (2006.01)

(52) U.S. Cl.
CPC ... *A61F 2/2427* (2013.01); *A61M 2025/0042* (2013.01)

(58) Field of Classification Search
CPC .................................................. A61F 2/2427
USPC ...................................................... 600/585
See application file for complete search history.

(56) References Cited

U.S. PATENT DOCUMENTS

| 4,854,330 | A  | * | 8/1989  | Evans, III | A61M 25/09 600/585 |
| 5,904,657 | A  | * | 5/1999  | Unsworth   | A61M 25/0155 600/434 |
| 6,206,834 | B1 | * | 3/2001  | Schwager   | A61B 5/0215 600/485 |
| 2008/0208329 | A1 | * | 8/2008  | Bishop  | A61B 17/10 623/2.11 |
| 2009/0265862 | A1 | * | 10/2009 | Guida    | C11D 3/046 8/109 |
| 2010/0256528 | A1 | * | 10/2010 | Lippert  | A61M 25/0013 600/585 |
| 2010/0298859 | A1 | * | 11/2010 | Miller   | A61M 25/0074 606/192 |
| 2011/0166648 | A1 | * | 7/2011  | Robin    | A61F 2/2418 623/2.1 |
| 2014/0155994 | A1 | * | 6/2014  | McDonald | A61F 2/2427 623/2.11 |
| 2015/0127093 | A1 | * | 5/2015  | Hosmer   | A61F 2/2418 623/2.11 |

* cited by examiner

*Primary Examiner* — Daniel L Cerioni
(74) *Attorney, Agent, or Firm* — Angela Holt; Bradley Arant Boult Cummings LLP

(57) ABSTRACT

A microcatheter device for crossing a patient's aortic valve has a guidetube combined with a free-floating and removable guidewire. The guidetube is generally hollow with a main shaft and a distal ring, the main shaft and the distal ring formed from flexible plastic. The distal ring is larger in diameter than the main shaft, and is configured to conform to an internal guidewire for insertion into the aorta, and then to deploy to form a downwardly-extending loop when in place in the left ventricle. A guidewire is received by the guidetube and is configured to advance into the distal ring to cause a diameter of the distal ring to expand, retract, or completely straighten. The distal ring diameter is thus adjustable to fit the size of the patient's left ventricle.

11 Claims, 2 Drawing Sheets

TAVR VALVE GUIDEWIRE AND GUIDETUBE WITH ADJUSTABLE DISTAL LOOP

REFERENCE TO RELATED APPLICATIONS

This application claims priority to Provisional Patent Application U.S. Ser. No. 62/301,270, entitled "TAVR Valve Guidewire and Guidetube with Adjustable Distal Loop" and filed on Feb. 29, 2016, which is fully incorporated herein by reference.

BACKGROUND AND SUMMARY

Current TAVR valve or other cardiac valve replacements require changing out multiple wires sequentially in order to guide replacement valves into the native aortic annulus. A first crossing wire is employed to cross the aortic valve, and then a valve delivery wire is employed to transport the valve into position. Multiple wires are required because the initial crossing of the aortic valve requires a relatively soft-tipped straight wire to advance through the valve; but a stronger wire is required to deliver the replacement valve. The valve delivery wire will have a large loop on the end for proper positioning in the ventricle.

These metal guidewires carry a risk to perforate the left ventricle and cause injury, complications, or death, so it would be desirable to have safer guidewires for a cardiac valve replacement.

The guidewire/guidetube combination according to the present disclosure reduces the complexity of the valve replacement procedure and cuts down on the number of wires required. Further, a microcatheter guidetube made of plastic surrounds the guidewire, and is less likely to cause perforations than the presently used bare metal guidewires.

DETAILED DESCRIPTION

Figure 1:
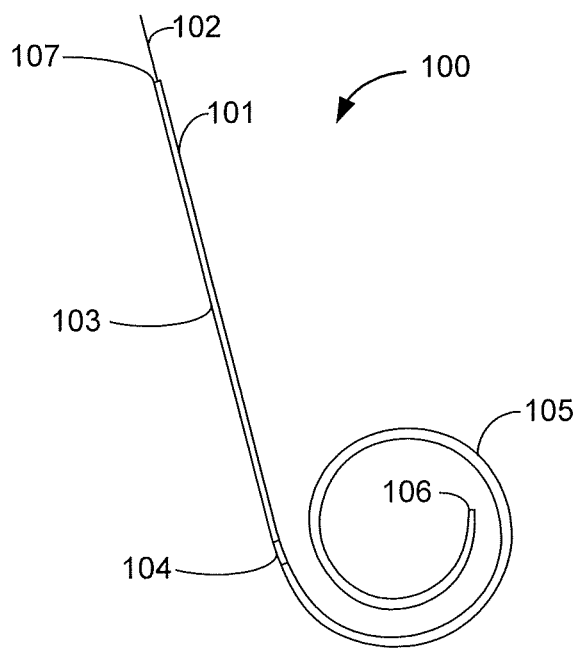
FIG. 1 depicts a guidetube and guidewire according to an exemplary embodiment of the present disclosure.

FIG. 1 depicts a microcatheter device 100 comprising a guidetube 101 combined with a free-floating and removable guidewire 102 according to the present disclosure. The guidetube 101 is a hollow microcatheter, formed from plastic in one embodiment. The guidetube 101 receives the guidewire 102, which slides within the guidetube 101 to advance and retract.

The guidetube 101 comprises a generally straight main shaft 103, a transition portion 104, and a distal loop 105. The distal loop 105 is disposed at a distal end of the guidetube 101. The distal loop 105 terminates at a distal opening 106 and a proximal opening 107.

The main shaft 103 is formed from kink-resistant, thin-walled, semi-rigid plastic tube that is 0.035 inches in outer diameter in one embodiment. In other embodiments, the main shaft 103 is formed with braided steel within the plastic of the guidetube.

The outer layer of the distal loop 105 is slightly larger in diameter than the main shaft 103, and in one embodiment is formed from kink-resistant, semi-rigid plastic tubing that is the range of 0.045-0.054 inches in outer diameter. The transition portion 104 transitions the main shaft 103 to the distal loop 105. In this regard, the main shaft 103 may be fused to the distal loop 105 at the transition portion 104.

The distal loop 105 being larger in diameter than the main shaft 103 helps to prevent excessive forward advancement of the valve delivery system (not shown) that delivers the replacement valve. In addition, the distal loop 105 being larger in diameter may simplify forming of the guidetube 101. In this regard, the main shaft 103 may be fit within and be frictionally received by the distal loop 105 prior to fusing of the main shaft 103 to the distal loop 105.

The distal loop 105 is softer than the main shaft 103, and when not acted upon by an external catheter (not shown) or the guidewire 102, the distal loop forms a loop as shown. In the illustrated embodiment, the body of the distal loop makes about one and one half loops. An outer diameter of the distal loop in this configuration may be about 3.0 centimeters.

Figure 2:
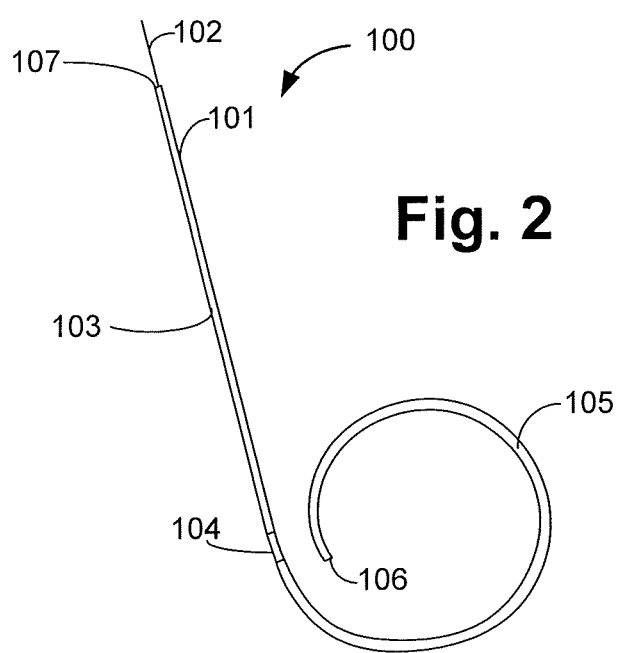
FIG. 2 depicts the guidetube and guidewire of FIG. 1, with the guidewire positioned such that the distal loop the guidewire is enlarged.

When the guidewire 102 is advanced such that its tip (not shown) enters the distal loop 105, the diameter of the distal loop 105 begins to increase. FIG. 2 illustrates the guidetube 101 with the guidewire 102 advanced such that the distal loop 105 has increased. In this configuration, the distal loop 105 now forms a larger loop. By advancing or retracting the guidewire 102, the size of the distal loop 105 may be enlarged or decreased, to more perfectly match the size of the patient's internal dimensions of the left ventricle.

Figure 3:
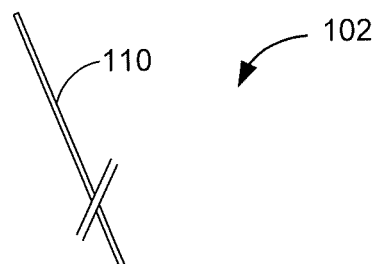
FIG. 3 depicts the tapered tip of the guidewire of FIG. 1, removed from the guidetube.

FIG. 3 depicts an exemplary guidewire 102 according to an embodiment of the present disclosure. The guidewire 102 is formed from flexible steel or alloy core wire in one embodiment. The guidewire 102 is advanced through the proximal opening 107 (FIG. 1) of the guidetube 101. In one embodiment, the guidewire 102 has a soft tip of plastic or metal.

The guidewire 102 comprises a main shaft 110 and a tapered distal tip 111. In this embodiment, the distal tip 111 is smaller in diameter than the main shaft 110. The distal tip 111 is the portion of the guidewire 102 that advances into the distal loop 105 (FIG. 1) of the guidetube 101 (FIG. 1). In another embodiment, the guidewire 102 is non-tapered with a soft distal tip. When a soft-tipped, straight guidewire (non-tapered) is employed, the guidewire 102 may extend slightly outside of the distal end of the guidetube 101. When a tapered distal end guidewire is employed, the guidewire stays within the guidetube 101.

Figure 4:
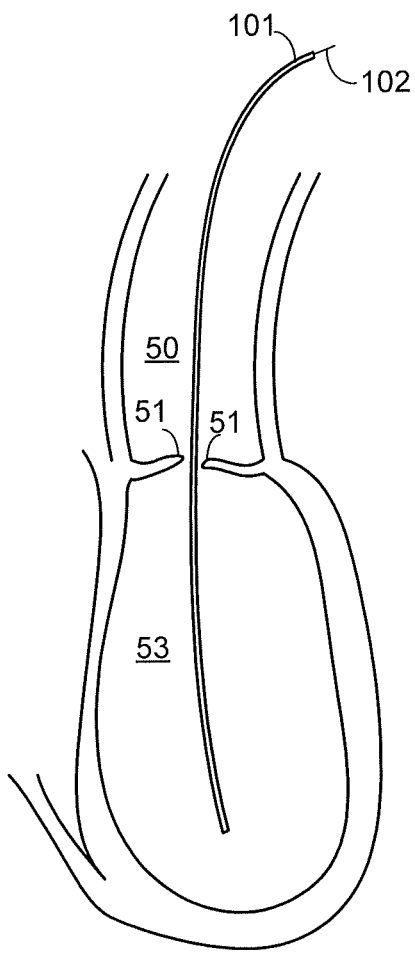
FIG. 4 depicts the guidewire/guidetube being advanced into across a patient's aorta.

FIG. 4 depicts the guidetube 101 and guidewire 102 being advanced into a patient's aorta 50 and through the aortic valve annulus 51. The guidetube 101 and guidewire 102 together are generally straight or slightly curved in this figure, because the guidewire 102 has been advanced fully into the guidetube 101 to straighten the guidetube 101 for advancement. When the guidetube 101 and guidewire 102 have been sufficiently advanced, the guidewire 102 is partially retracted to deploy the distal loop 105 of the guidetube 101.

Figure 5:
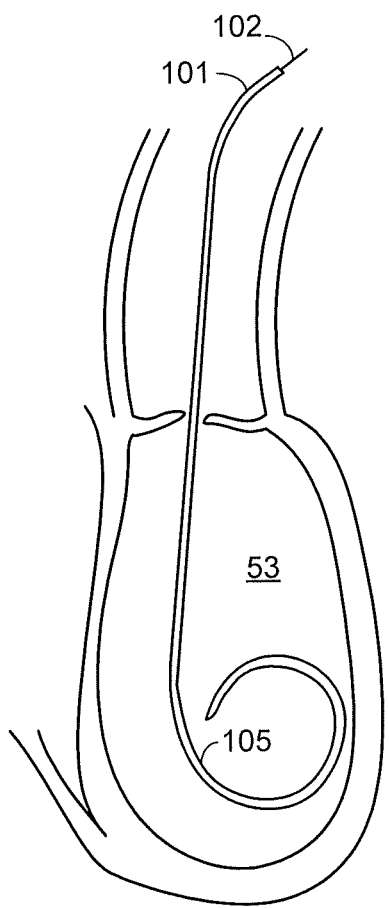
FIG. 5 depicts the distal loop of the guidetube being deployed in the patient's left ventricle.

FIG. 5 depicts the distal loop of the guidetube deployed in the patient's left ventricle 53. As discussed above, the diameter of the distal loop is adjustable by advancing or retracting the guidewire 101, to accommodate the size of the patient's left ventricle 53.

This disclosure may be provided in other specific forms and embodiments without departing from the essential characteristics as described herein. The embodiments described are to be considered in all aspects as illustrative only and not restrictive in any manner.

What is claimed is:

1. A method of positioning a cardiac valve, the method comprising:
   advancing a microcatheter into a patient's aorta, across the patient's aortic valve, and downwardly into the patient's left ventricle cavity, the microcatheter comprising:
   a generally hollow guidetube comprising a main shaft and a distal ring, the main shaft and the distal ring formed from flexible plastic tubing, the tubing of the distal ring larger in diameter than the tubing of the main shaft, the distal ring configured to conform to a guidewire for insertion into the aorta, and to deploy to form a downwardly-extending, substantially circular loop when in place in the left ventricle, and
   the guidewire received by the guidetube, the guidewire stiffer than the guidetube, such that advancing the guidewire into the distal ring causes a diameter of the distal ring to expand, and such that retraction of the guidewire causes the diameter of the distal ring to contract;
   retracting the guidewire until the guidetube deploys to form a downwardly-extending, substantially circular distal ring within the patient's left ventricle cavity, the downwardly-extending, substantially circular distal ring formed in a single plane;
   partially advancing the guidewire to increase the diameter of the distal ring to a desired diameter.

2. The method of claim 1, wherein advancing the guidewire fully into the distal ring straightens the distal ring to conform to the guidewire.

3. A method of positioning a cardiac valve, the method comprising:
   advancing a microcatheter into a patient's aorta, across the patient's aortic valve, and downwardly into the patient's left ventricle cavity, the microcatheter comprising: a generally hollow guidetube comprising a main shaft and a distal ring, the main shaft and the distal ring formed from flexible plastic tubing, the distal ring configured to conform to an internal guidewire for insertion into the aorta, the internal guidewire and the distal ring generally straight when inserted into the aorta, the distal ring further configured to deploy to form a downwardly-extending, substantially circular loop when in place in the left ventricle, the internal guidewire received by the guidetube, the internal guidewire stiffer than the guidetube, such that advancing the guidewire into the distal ring causes a diameter of the distal ring to expand, and such that retraction of the guidewire causes the diameter of the distal ring to contract;
   retracting the internal guidewire until the guidetube deploys to form a downwardly-extending, substantially circular distal ring;
   partially advancing the internal guidewire to increase the diameter of the distal ring to a desired diameter.

4. The method of claim 3, wherein advancing the guidewire fully into the distal ring straightens the distal ring to conform to the guidewire.

5. The method of claim 3, the tubing of the distal ring larger in diameter than the tubing of the main shaft.

6. The method of claim 1, wherein the step of retracting the guidewire until the guidetube deploys to form a distal ring of a desired diameter further comprises the desired diameter of the distal ring substantially matching the size of the patient's left ventricle cavity.

7. The method of claim 3, wherein the step of retracting the guidewire until the guidetube deploys to form a distal ring of a desired diameter further comprises the desired diameter of the distal ring substantially matching the size of the patient's left ventricle cavity.

8. The method of claim 1, the distal ring comprising substantially one and one half loops when deployed, with the guidewire fully retracted from the guidetube.

9. The method of claim 1, the distal ring comprising substantially one loop when deployed, with the guidewire partially advanced into the guidetube.

10. The method of claim 3, the distal ring comprising substantially one and one half loops when deployed, with the guidewire fully retracted from the guidetube.

11. The method of claim 3, the distal ring comprising substantially one loop when deployed, with the guidewire partially advanced into the guidetube.

* * * * *